US009155472B2

(12) United States Patent
Gebicki et al.

(10) Patent No.: US 9,155,472 B2
(45) Date of Patent: Oct. 13, 2015

(54) METHOD FOR EVALUATING VASCULAR ENDOTHELIUM FUNCTION AND A SYSTEM THEREFOR

(75) Inventors: Jerzy Gebicki, Lodz (PL); Andrzej Marcinek, Lodz (PL); Stefan Chlopicki, Kraków (PL)

(73) Assignee: Angionica SP. Z O.O., Lodz (PL)

( * ) Notice: Subject to any disclaimer, the term of this patent is extended or adjusted under 35 U.S.C. 154(b) by 685 days.

(21) Appl. No.: 13/483,625

(22) Filed: May 30, 2012

(65) Prior Publication Data

US 2012/0310057 A1    Dec. 6, 2012

Related U.S. Application Data

(60) Provisional application No. 61/491,543, filed on May 31, 2011.

(51) Int. Cl.
A61B 5/1455 (2006.01)
A61B 5/00 (2006.01)
A61B 5/145 (2006.01)
A61B 5/02 (2006.01)

(52) U.S. Cl.
CPC ........... *A61B 5/0071* (2013.01); *A61B 5/02007* (2013.01); *A61B 5/14546* (2013.01); *A61B 5/7271* (2013.01); *A61B 5/441* (2013.01)

(58) Field of Classification Search
CPC .... A61B 5/14546; A61B 5/1455; A61B 5/72; A61B 5/7271; A61B 5/0071; A61B 5/02007
See application file for complete search history.

(56) References Cited

U.S. PATENT DOCUMENTS

| | | | | |
|---|---|---|---|---|
| 5,685,313 A | * | 11/1997 | Mayevsky | 600/478 |
| 6,711,424 B1 | * | 3/2004 | Fine et al. | 600/322 |
| 8,473,036 B2 | * | 6/2013 | Gorman et al. | 600/476 |
| 2004/0054270 A1 | * | 3/2004 | Pewzner et al. | 600/341 |
| 2008/0183059 A1 | | 7/2008 | LaPlante et al. | |
| 2010/0292592 A1 | | 11/2010 | Parfenov et al. | |

OTHER PUBLICATIONS

Written Opinion of the International Searching Authority (ISA/O.E.P.M.) on Nov. 12, 2012 in connection with International Application No. PCT/IB2012/052691.

* cited by examiner

*Primary Examiner* — Eric Winakur
(74) *Attorney, Agent, or Firm* — Gary J. Gershik; Cooper & Dunham LLP

(57) ABSTRACT

A method for evaluating vascular endothelium function in a human subject comprises monitoring changes in intensity of NADH fluorescence signal emitted from skin tissue cells of an upper limb of said subject as a function of time, wherein said changes result from reactive hyperaemia caused by blocking and releasing blood flow in the same upper limb of said subject. A system for evaluating vascular endothelium function in a human subject comprises a means for illuminating a skin on an upper limb of said subject with exciting light, a means for measuring intensity of fluorescence signal emitted from the skin and recording changes of said intensity of the fluorescence signal over time; and a restriction means for blocking and releasing blood flow in the upper limb of said subject.

21 Claims, 4 Drawing Sheets

METHOD FOR EVALUATING VASCULAR ENDOTHELIUM FUNCTION AND A SYSTEM THEREFOR

This application claims benefit of U.S. Provisional Application No. 61/491,543, filed May 31, 2011, the content of which is hereby incorporated by reference into the present application.

THE FIELD OF THE INVENTION

The present invention relates to a non-invasive method for evaluating vascular endothelium function and a system for performing said method.

THE BACKGROUND ART

Vascular endothelium is a cellular layer lining the inner part of blood vessels, including arteries and veins. Endothelium is presently looked upon as an important metabolically active autocrine/paracrine/endocrine organ that regulates cardiovascular function and maintains vascular homeostasis by: modulating vascular tone; regulating solute transport into cell components of the vessel wall, local cellular growth, and extracellular matrix deposition; protecting the vessel from the potentially injurious consequences of substances and cells circulating in blood; and regulating the hemostatic, inflammatory, and reparative responses to local injury. One of the main functions of endothelium is to produce or release substances, such as nitric oxide (NO), that control the behaviour of the blood vessels such as their dimensions, elasticity, permeability and reactivity, including the ability to constrict and dilate. Endothelium-derived mediators regulate not only blood flow and permeability vascular elasticity, reactivity and structure, but also local and systemic inflammatory response as well as thromboresistance of vessels. Vasoprotective endothelial mediators such as nitric oxide (NO), prostacyclin (PGI2) endothelium-derived hyperpolarising factor (EDHF), bradykinin (Bk) tissue plasminogen activator (t-PA), thrombomodulin (TM) or ADP-ase do exert antithrombotic, anti-inflammatory and vasoprotective action.

On the other hand, excessive production by endothelium of superoxide anions (O2-), isoprostanes, angiotensin II (ang II), endothelin 1 (ET-1), plasminogen activator inhibitor (PAI-1), tissue factor (TF), von Willebrandt factor (vWF), chemokines (e.g. monocyte chemotactive protein MCP-1), cytokines (e.g. IL-6), and increased expression of adhesion molecules (e.g. selectin P, ICAM-1) promote inflammation and thrombosis of vascular wall that may eventually lead to the development of atherosclerotic lesion. Accordingly, healthy endothelium is essential for undisturbed functioning of the cardiovascular system, while endothelial dysfunction leads to its various pathologies. In particular, endothelial dysfunction is pivotal to atherogenesis, it is present at the earliest stages (e.g. preceding angiographic or ultrasonic evidence of obstructive plaque) as well as later stages of arterial disease, contributing to clinical sequelae related to tissue damage (eg, ischemia, infarction, and organ failure).

Endothelial dysfunction in most general terms refers to an impairment of the ability of the endothelial cell layer to produce an appropriate vasodilatory response to stimuli. Many studies provided evidence that endothelial dysfunction (assessed on the basis of the impairment of NO-dependent vasodilatation) may be regarded as prognostic factor for the development of adverse cardiovascular events. Indeed, relative risk for adverse outcomes is elevated approximately 10-fold when there is evidence of coronary or peripheral endothelial dysfunction.

Various conditions, including hypercholesterolemia, systemic hypertension, smoking, diabetes, congestive heart failure, pulmonary hypertension, estrogen deficiency, hyperhomocysteinemia, and the aging process itself, have been associated with impaired function (dysfunction) of endothelium. As a result, the vessel wall in these conditions may promote inflammation, oxidation of lipoproteins, smooth muscle proliferation, extracellular matrix deposition or lysis, accumulation of lipid-rich material, platelet activation, and thrombus formation. All of these consequences of endothelial dysfunction may contribute to development and clinical expression of atherosclerosis. The potential consequences of endothelial dysfunction further include coronary constriction or inadequate dilation during physical or mental stress, producing myocardial ischemia; plaque rupture and thrombosis, causing unstable angina or myocardial infarction; and reperfusion injury after thrombolysis.

Several methods and apparatuses for non-invasive evaluation of the health of vascular endothelium in vivo have been developed.

In particular, methods are known that are based on monitoring the physiological conditions or characteristics of the arteries in the patient's limb after reactive hyperemia.

Reactive hyperemia is a physiological phenomenon that occurs in a patient after blocking (or occlusion) of a major artery. Such blocking or occlusion of artery in the limb, such as brachial artery, is typically done by inflating a blood pressure cuff slightly above systolic pressure for a period of about 5 minutes. Anoxia or severe hypoxia in the limb downstream from the occluded artery is usually a result of such blocking. Sudden release of the blocking causes endothelial cells to react by generating NO and dilating. The phenomenon of reactive hyperemia lasts up to 10 minutes before return to pre-test blood volume values. Blood flow is a characteristic of the artery, and under reactive hyperemia blood flow through an artery, vein or limb is significantly greater as compared with normal blood flow.

Currently the most popular method is flow mediated dilatation (FMD), a non-invasive technique based on monitoring of diameter of arteries after reactive hyperemia with a two-dimensional ultrasound and Doppler ultrasound. Its results correlate well with invasive coronary endothelial testing as well as with the presence and severity of coronary atherosclerosis. This technique is described for example in a review by S. Patel. And D. S. Celermajer, Pharmacological Reports 2006, 58, suppl. 3-7. However, this method is quite expensive, requires sophisticated equipment and highly specialized operators, is highly operator dependent and is poorly reproducible due to variability of measurements and poor resolution relative to arterial size. Hence, its use is limited and the method is not applicable on a more general basis.

For the purpose of assessment of vascular endothelial function changes of other physical parameters in response to reactive hyperemia have been also used, such as fingertip skin temperature (WO2005118516; N. Ahmadi et al. Int. J. Cardiovasc. Imaging (2009) 25:725-738), blood pressure in a finger (pulse wave amplitude) using plethysmography (EP1360929, EP1992282, WO00/57776, EP2110074), and peripheral arterial tone (WO2000/074551, WO2002/034105).

Non-invasive technique for detection of endothelial dysfunction based on monitoring blood flow related changes in the level of a substance present in a limb after reactive hyperemia is disclosed in WO03/051193. The method involves blocking blood flow in the limb to stimulate endothelial function and then releasing the blood flow block to observe, measure and record said changes as a function of time, said changes being indicative of endothelial dysfunction. Said substance can be a tracer substance injected in a vein, such as a radiation emitter or a contrast agent, and the ingress of said tracer into the limb is detected and measured, for example by means of gamma ray detection. Tracer measurement in a pair of two laterally opposed limbs should be performed and the tracer presence compared between both limbs. Alternatively, a physical characteristics of the limb, such as temperature or color, or a property of a metabolic or other biochemical product circulating in the limb following the release of the blood flow block, such as $O_2$, $CO_2$ or reduced hemoglobin, is measured by a suitable technique. As suitable techniques there were suggested gas emissions across the skin surface within a cell placed on the skin surface, optical techniques, such as spectral analyzers or optical transmission/diffusion detectors, such as the visible-reflectance hyperspectral analysis, and EPR/NMR techniques. Either the appearance rate of a depleted substance or the disappearance (depletion) of an accumulated product can be detected. A rate of change of the measured parameter shortly after release of the occlusion or blockage is suggested as a primary factor in determining endothelial dysfunction. In the case of the use of a tracer, the rate for both the blocked limb and the contra-lateral control limb is measured.

It has been established that endothelial dysfunction is an early event and major risk factor for atherosclerosis and an important indicator for a medical professional, allowing for early diagnosis of the risk of cardiovascular disease.

Testing endothelial function is therefore a highly desirable alternative for a diagnostic approach based on performing a set of various biochemical tests, especially in apparently healthy individuals, i.e. individuals not showing any signs of cardiovascular disease.

A testing method is needed that would allow to evaluate function and detect any dysfunctions at an early stage of impairment in order to identify patients for prophylactic or therapeutic intervention to improve the dysfunction and/or for further more detailed and complicated diagnostic tests.

The need exists to provide a non-invasive test for evaluating endothelial function which would be reliable, easy to carry out and inexpensive, and thus applicable for tests in large patient populations, for example for screening purposes.

There is also a need for a simple, quick and non-expensive test that would allow to monitor and control the response of a patient to a medical treatment of cardiovascular disease.

SUMMARY OF THE INVENTION

Such a test is provided by the present invention, which relates to a method and a system for non-invasive and simple evaluation of function of vascular endothelium by monitoring intensity of NADH fluorescence signal emitted from skin tissue cells on an upper limb upon illumination with UV light and changes of said intensity of said fluorescence signal as a function of time in response to blocking and releasing blood flow in the upper limb to cause reactive hyperemia.

The present invention provides also a system for evaluating vascular endothelium function in a human subject using said method.

The invention will be described below in more detail with reference to the attached Figures of the drawing.

DETAILED DESCRIPTION OF THE INVENTION

Figure 1:
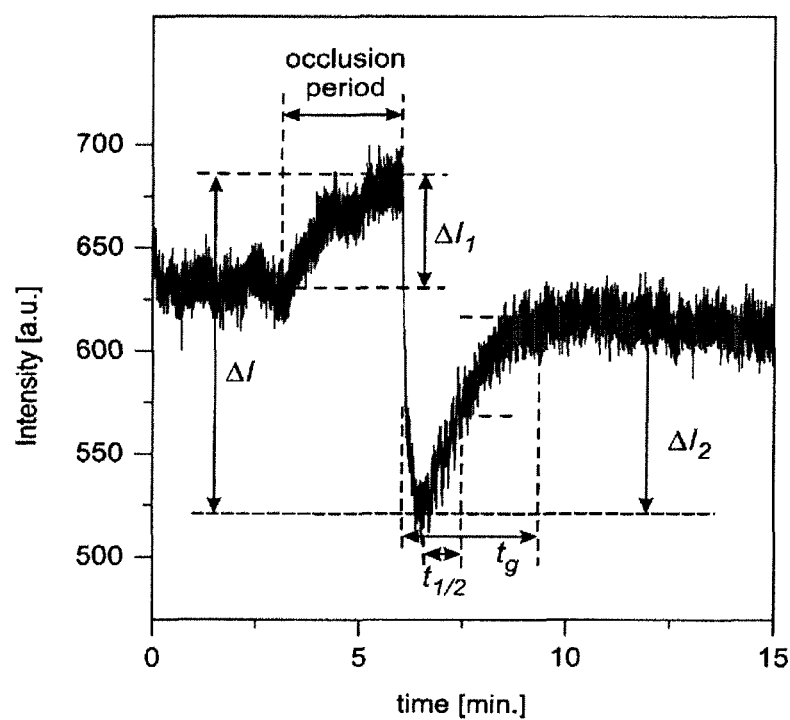
FIG. 1 shows the exemplary course of the recorded intensity of NADH fluorescence signal versus time with characteristic parameters of the curve.

The present invention provides a method for evaluating vascular endothelium function in a human subject, the method comprising:
 (a) measuring and recording as a function of time the intensity of NADH fluorescence signal emitted from skin tissue cells in a selected location on an upper limb of said subject to obtain a baseline;
 (b) blocking blood flow to the upper limb upstream to the selected location, while continuing measuring and recording said intensity as it grows up as a function of time;
 (c) releasing the block of blood flow while continuing measuring and recording said intensity as it changes as a function of time until obtaining a stationary state; and
 (d) determining parameters indicative of endothelial function from the course of changes of said intensity.

In another aspect, the invention relates to the method of determination of parameters for evaluation of vascular endothelium function in a human subject, the method comprising:
 (a) measuring and recording as a function of time the intensity of NADH fluorescence signal emitted from skin tissue cells in a selected location on an upper limb of said subject to obtain a baseline;
 (b) blocking blood flow to the upper limb upstream to the selected location, while continuing measuring and recording said intensity as it grows up as a function of time;
 (c) releasing the block of blood flow while continuing measuring and recording said intensity as it changes as a function of time until obtaining a stationary state; and
 (d) determining parameters indicative of endothelial function from the course of changes of said intensity.

Intensity of NADH fluorescence signal emitted from skin tissue cells in a selected location on the upper limb, such as on forearm, hand or a finger is measured and recorded. In a preferred embodiment, the selected location is forearm or hand, such as dorsal or palmar side of the hand (back of the palm or interior of the palm).

It will be appreciated by a skilled person that the NADH fluorescence signal is emitted by cellular NADH upon illumination with and absorption of UV light by the tissue.

It will be also appreciated by a skilled person that the NADH fluorescence signal will be measured at the location downstream of the blockage of blood flow in the limb. In other words, the blood flow will be blocked and released upstream to the place of measurement and monitoring of NADH fluorescence.

The wavelength of excitation light will be at the UV range absorbed by NADH, i.e. 300 to 400, preferably 315 to 400, more preferably 340-360 nm, most preferably 350±5 nm.

The wavelength of the fluorescence light will be at the range emitted by NADH after absorption of excitation light, i.e. 420 to 480, preferably 450-470 nm, most preferably 460±5 nm.

Therefore, the method of the invention comprises illumination of a selected location on the upper limb of the subject, such as on a forearm, hand or a finger, preferably forearm or hand, with UV light and continuous measurement and recording intensity of emitted NADH fluorescence signal and its changes as a function of time at a plurality of points in time before, during and after blocking blood flow and then releasing the block of blood flow upstream to said selected location to cause reactive hyperemia. Then, parameters or data indicative of endothelial function are determined from said changes.

The monitoring of the intensity of NADH fluorescence signal in method of the invention is typically performed in the following manner.

In step (a) measurement and recording of said intensity of NADH fluorescence signal is performed over a first period of time prior to blocking blood flow to obtain a baseline.

Said measurement and recording in said first period of time in step (a) lasts sufficiently long to record a steady baseline of the fluorescence intensity level.

Usually, it is sufficient to record a baseline for a period of up to 1 to 2 minutes, typically for about 2 minutes. It will be appreciated by a skilled person that depending on circumstances longer time may be required to obtain a steady baseline, such as up to 3 minutes, up to 4 minutes or up to 5 minutes.

Then, after obtaining a baseline, in step (b) blood flow in the upper limb is blocked, as described above, while the measurement and recording the intensity NADH fluorescence signal is continued over a second period of time, during which second period the intensity of NADH fluorescence signal grows up to reach its maximum level. In some subjects, upon reaching maximum level the intensity may additionally stabilize at this level for a certain time. Usually, this second period of time in step (b) lasts up to 5 minutes, such as 1, 2, 3, 4 or 5 minutes.

Subsequently, in step (c) the blockage of blood flow is released and the measurement and recording is continued over a third period of time upon releasing the block of blood flow, during which third period the intensity NADH fluorescence signal decreases from its maximum level reached in step (b) to reach minimum level and grows up from said minimum level again until a new stationary level of said fluorescence level is obtained. This new stationary level corresponds essentially to the initial baseline determined in step (a) before blocking the blood flow. Usually, this third period of time lasts up to 15 minutes, such as 5, 6, 7, 8, 9, 10, 11, 12, 13, 14 or 15 minutes, preferably 2 to 7 minutes.

Thus, the whole time period of measuring and recording is typically up to 25 minutes, usually up to 20 minutes.

The method of the invention requires blocking the blood flow in the upper limb by means of occlusion of an artery, such as brachial artery. It will be appreciated that for the purpose of the present specification the term "blocking" refers to the mechanical blocking applied externally to the limb of a subject and has the same meaning as the term "occlusion" and both terms can be used interchangeably with each other.

It will be understood that by releasing the block of blood flow the blood flow in the vasculature of the upper limb is restored. Thus, the terms "releasing blood flow" and "releasing the block of blood flow" have the same meaning and refer to the restoration of blood flow after occlusion of an artery by means of releasing mechanical means blocking the flow.

In the method of the invention, said blocking and releasing the block of blood flow can be advantageously obtained by tightening and releasing, respectively, a restriction means around said upper limb.

Preferably, such tightening and releasing is performed around the brachial artery in the upper limb (arm).

Said restriction means can be any means capable of tightening around the limb, such as tightening hoop or band.

Preferably, however, said restriction means is an inflatable restriction means, most preferably an inflatable pressure cuff, such as sphygmanometer cuff.

Preferably, said inflatable pressure cuff, such as sphygmanometer cuff, is inflated to the pressure above systolic pressure of the subject undergoing examination, such as 50 mm above the systolic pressure.

In one embodiment of the method of the invention the release of the tightening means around the limb will be done quickly (rapidly), and preferably will be done automatically.

In one embodiment the measurement will be performed on a forearm or a dorsal or palmar side of a hand of the subject.

Another object of the present invention is a system for performing evaluation of vascular endothelium function in a human subject in accordance with the method of the invention as defined above.

The system of the invention comprises a means for illuminating a skin of the upper limb of said subject with the exciting light at the range of 300 to 400 nm, a means for detecting and measuring intensity of fluorescence signal from said skin, a means for measuring and recording changes of intensity of said fluorescence signal as a function of time, as well as restriction means for blocking and releasing blood flow in the upper limb of said subject.

Techniques of obtaining, detecting, measuring and recording NADH fluorescence signal from tissue cells (NADH fluorometry) are well known in the art and any conventional fluorometer apparatus or system can be used to perform the method of the invention.

Said means for illuminating, detecting, measuring, recording and plotting as mentioned above can be integrated in such a fluorometer.

Generally, the fluorometer apparatus or system should be at least equipped with:

- a source of excitation light capable of emitting UV light in the range absorbed by NADH, i.e. at the wavelength range of 300 to 400 nm;
- a probe to be placed at the selected location close to the skin of the subject, with a light guide capable of carrying the excitation light signal from the source of light to the selected location;
- a fluorescence collector for receiving a fluorescence emitted from said tissue;
- a detector of fluorescence signal at least in the range emitted by NADH, i.e. at the wavelength range of 400 to 600 nm;
- a signal processing unit; and
- a recording/plotting unit for recording a fluorescence curve.

Generally, there is a great flexibility in configuration of the apparatus, provided that all essential elements listed above are included.

Conventional sources of excitation light known in the art can be used, including filtered spectral lamp such as mercury or xenon lamp, light emitting diode LED, laser diode or pulsed laser. Advantageous source of is the light emitting diode LED.

Any conventional light guide can be used for carrying excitation light and for collecting, such as optical fibres, optionally in a flexible housing.

The probe with the light guide will be placed close to the skin, either in direct contact with the skin or in close vicinity to the skin.

In one embodiment, the measurement will be performed on a forearm or the palmar side of a hand and the light guide will be carried to the support for placing hand or to the band fixed on the hand.

In another embodiment, the measurement will be performed on the dorsal side of a hand placed on a support, such as tripod, and a stiff light guide will be fixed above the hand.

In another embodiment, the measurement will be performed on a finger, by means of a cup, a hoop or a cuff at the end of the light guide, said cup, hoop or cuff being tightened around the finger depending on the size of the latter.

In yet another embodiment the measurement will be performed in a multipoint manner. For example, several light-guides can be carried to the band mounted around a forearm or a finger.

Conventional detectors can be used, such as photodiode detector, fast photodiode detector, photon multiplier tube, etc.

Typical signal processing units recording units known in the art can be used for plotting the curve of intensity of NADH fluorescence.

It is known that nicotinamide adenine dinucleotide ($NAD^+$), found in all existing cells and playing essential role in metabolism as a co-enzyme in redox reactions, in its reduced form i.e. NADH, absorbs UV light at almost the entire UVA spectrum area at the 300 to 400 nm range and in response to illumination with UV light emits fluorescence light at the 400 to 600 nm range, with a peak at about 480 nm. Intensity of the NADH fluorescence is proportional to the concentration of mitochondrial NADH. This phenomenon is the foundation of the technique of diagnosing mitochondrial function (i.e. energy production) and tissue or organ vitality in vivo by real-time measurement and monitoring of mitochondrial NADH fluorescence, in combination with examination of other additional parameters, depending on the selected monitored organ. When monitoring mitochondrial function is performed in a blood-perfused organ in vivo, NADH fluorescence signal is affected by changes of tissue blood volume. These hemodynamic artifacts have to be eliminated from the measured fluorescence signal using the reflectance signal from the illuminated tissue, which dependent on blood volume changes, and suitable algorithms. The method and a device—fluorometer/reflectometer for such monitoring is described for example in WO/2002/024048 and in A. Mayevsky et al., J. of Biomedical Optics 9(5), 1028-1045 (2004).

Without the intention of being bound by theoretical considerations, it is believed that in the method of the invention, in the absence of influence of physical factors, the intensity of NADH fluorescence emitted in vivo from skin tissue cells is proportional to the concentration of mitochondrial NADH (the reduced form). Any change in the redox status of $NAD^+$/NADH system caused by the change of the oxygen supply will be reflected in the intensity of the emitted fluorescence.

Decrease in the supply of oxygen with the blood to the tissue due to blocking of blood flow in the vasculature by occlusion of the artery shifts the redox equilibrium towards a more reduced state, this resulting in the increase of the measured level of intensity of NADH fluorescence to the new equilibrium above the initial baseline. Release of the flow blockage causes rapid increase in the supply of oxygen with blood to the cells and a shift of the redox equilibrium towards a less reduced state, thus decreasing the measured level of intensity of NADH fluorescence. NADH fluorescence may decline initially below the baseline level and then again increase to reach the equilibrium and return to a stationary state corresponding essentially to the initial baseline level of fluorescence.

In the method of the invention, the initial intensity of fluorescence in the stationary state (baseline) varies from one individual to another and may depend to a certain extent on such factors like fitting of the measurement system (especially a probe) to the limb, the state and colour of the skin, etc. and is a reference for further observations in the same person. Differences in the baseline fluorescence can be used for calibration of the method for comparison of the results obtained for different patients.

As the baseline intensity of the fluorescence signal is measured in relative, apparatus-related units, which may depend on such factors as for example intensity of exciting light, efficiency of a light-guide, geometry of the measurement, it is comparable for the same apparatus and different patients. Differences in the baseline fluorescence can be used for calibration of measurements for different apparatus or upon technical modification of the system.

Return of the fluorescence level to the stationary state corresponding essentially to the initial baseline observed during the test in accordance with the method of the invention is not only due to return of cellular metabolic processes to the initial equilibrium, since such equilibrium of metabolic processes is reached in much shorter time of less than one minute. Unexpectedly and surprisingly, the time span of the process observed in the method of the invention is longer and is mainly dependent on physical changes connected with the increase of the blood flow and later restoration of the original equilibrium.

The time span and the rate of return of the fluorescence level after releasing the block of blood flow in step (c) to the stationary state corresponding essentially to the initial baseline level of step (a) are measures of response of vascular system and the ability of endothelium to perform its function of constriction and dilatation and allow to assess the functioning of the endothelium.

The half-time of the increase of the intensity of fluorescence signal level after releasing the block of blood flow in step (c) from its minimum level to the stationary state shows kinetics of the process of the return to the stationary state and is an additional measure of the endothelial function.

Therefore, the following parameters of the curve intensity vs. time, as shown on FIG. 1, are indicators of functioning of the vascular endothelium, i.e. its propensity to properly restrict and dilate in response to various stimuli:

- the difference $\Delta l$ between the maximum level of intensity of NADH fluorescence signal upon blocking blood flow in step (b) and the minimum level of intensity of NADH fluorescence after releasing the block of blood flow in step (c);
- the difference $\Delta l_1$ between the baseline intensity of NADH fluorescence signal in step a) prior to blocking blood flow and the maximum level of intensity of NADH fluorescence signal in step (b) upon said blocking;
- the difference $\Delta l_2$ between the minimum level of intensity of NADH fluorescence signal and its level at the stationary state after releasing the block of blood flow in step (c);
- the time span ($t_g$) from releasing the block of blood flow in step (c) till return of the intensity of NADH fluorescence signal to the stationary level in step (c), corresponding essentially to the baseline of step (a) prior to blocking blood flow;
- the half-time ($t_{1/2}$) required for increase of the intensity of NADH fluorescence signal from its minimum value after releasing the block of blood flow in step (c) by a half of the difference ($\Delta l_2$) as defined above, i.e. the difference between the minimum level of intensity of NADH fluorescence signal and its level at the stationary state after releasing the block of blood flow in step (c).

The invention will be described in more detail in the following Examples

EXAMPLE 1

NADH fluorescence from skin cells of the hand of a human subject and changes of intensity of this fluorescence accompanying occlusion of the brachial artery and release of blood flow were measured. The health of the subject was not examined.

The measurement was performed using Carry Eclipse fluorescence spectrophotometer equipped with a xenon flash lamp, a fibre optic system with a probe suitable for measuring the emission from the surface of a solid and a PMT detector.

The wavelength of the excitation light was 350 nm and the wavelength of monitored emission signal was 460 nm.

Intensity of a fluorescence signal from the dorsal side of the palm of the subject between thumb and the index finger ("pointer" finger) was registered for 2 minutes (first time period), during which time a stationary state corresponding to initial baseline was reached.

After 2 minutes the blood flow in the brachial artery of the same hand was blocked by inflating and tightening the inflatable sphygmanometer cuff around the subject's arm above the systolic pressure for a second period of time–occlusion period.

Measurement of the intensity of the fluorescence signal was continued for further 4 minutes period (second period of time–occlusion period), during which the increase of the fluorescence signal was observed starting from the point of time of tightening the cuff.

After 4 minutes the sphygmanometer cuff was quickly released by deflating and the measurement of intensity of the fluorescence signal was continued for further 14 minutes period (third period of time). Rapid decrease of the fluorescence signal to the minimum level was first observed upon releasing the cuff, followed by gradual increase of the signal until the stationary state corresponding essentially to the level of initial baseline recorded in the first period.

FIG. 1 shows the course of the fluorescence signal intensity curve recorded during the measurement described above and determination of parameters of the curve characteristic for the function of the vascular endothelium.

The values of the parameters $\Delta l$, $\Delta l_1$ and $\Delta l_2$ as defined above were measured.

Also, the time-span $t_g$ and the half-time $t\frac{1}{2}$ as defined above were determined from the plot of the curve.

Figure 2:
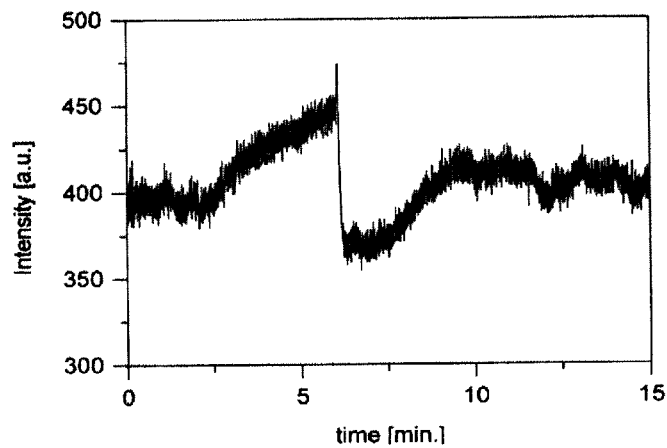
FIGS. 2 to 7 show the records of the curves of intensity of NADH fluorescence signal in tested subjects.
Figure 3:
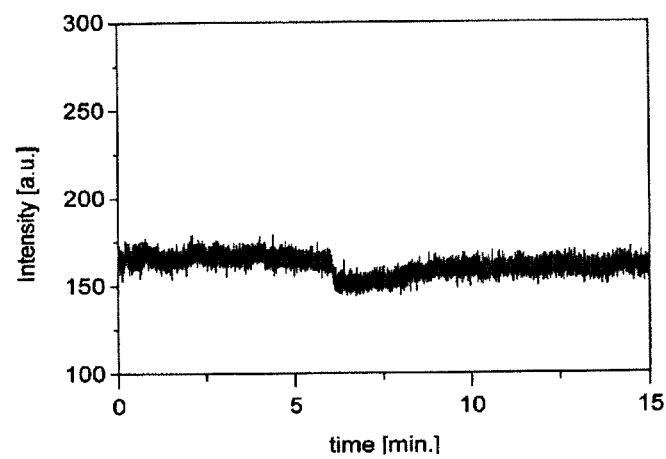
Figure 4:
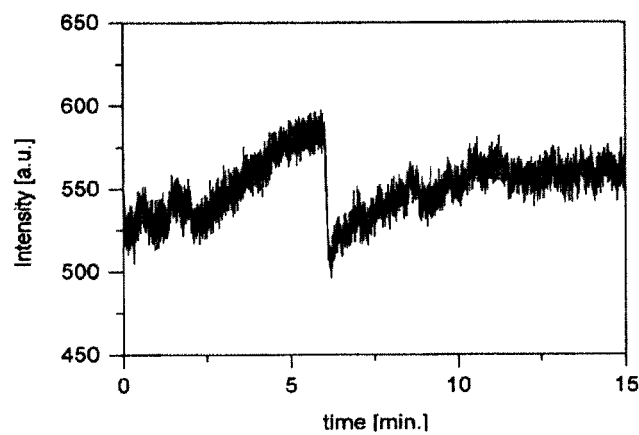
Figure 5:
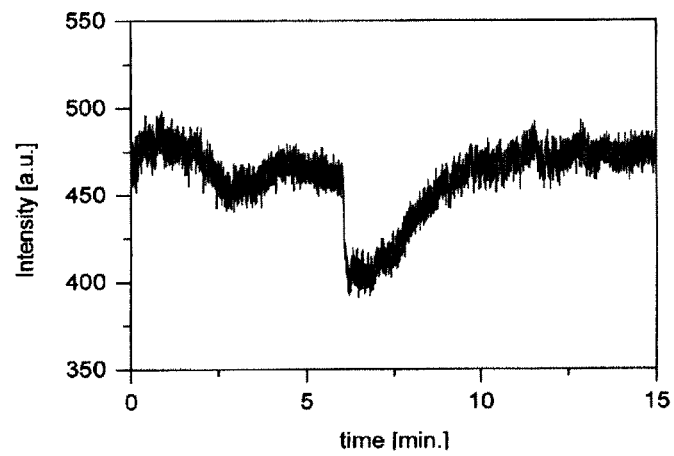
Figure 6:
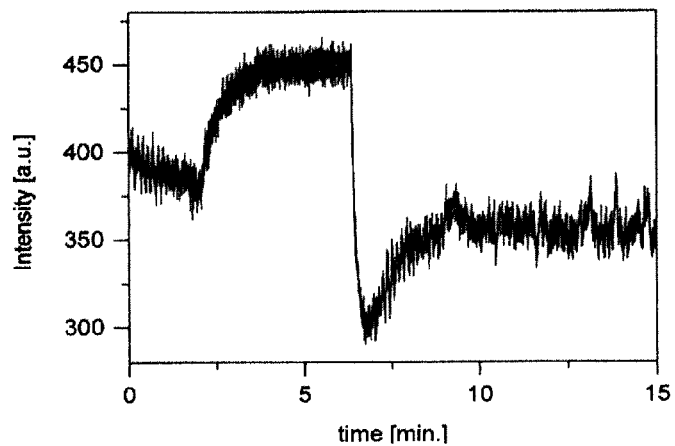
Figure 7:
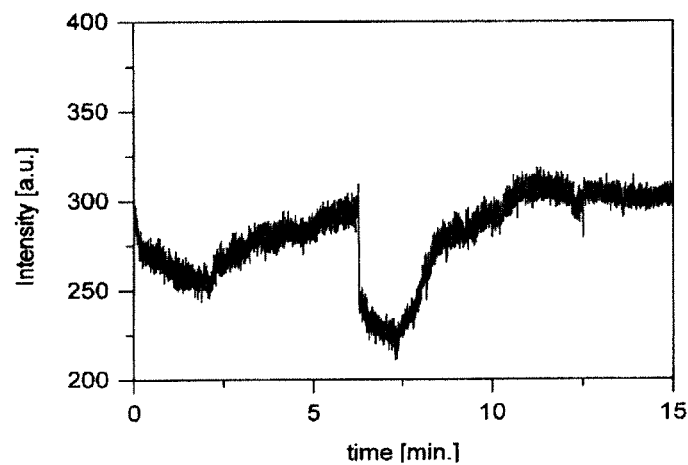

In the same manner as described above, measurements were performed for:
- a non-smoking, 27-year-old person, with the record of the fluorescence curve shown on FIG. 2;
- a non-smoking, 71-year-old person, with the record of the fluorescence curve shown on FIG. 3;
- a non-smoking, 32-year-old person, with the record of the fluorescence curve shown on FIG. 4;
- a smoking, 26-year-old person, with the record of the fluorescence signal shown on FIG. 5;
- a non-smoking, 28-year-old person, with the record of the fluorescence signal shown on FIG. 6; and
- a smoking, 53-year-old person, with the record of the fluorescence signal shown on FIG. 7.

As it can be seen, the records of the intensity curves differ between patients.

The record of the curve for an aged person (FIG. 3), with a very small decrease after occlusion of the blood flow (difference between the baseline and the minimum intensity value) and very slow rate of return to the stationary state after release of the occlusion, shows bad functioning of vascular endothelium.

The records for smoking persons (FIGS. 5 and 7), with small rates of return to the stationary state, show impaired functioning of vascular endothelium.

The records of two young non-smoking patients shown on FIGS. 4 and 6 show differences in the functioning of vascular endothelium, with higher return rate for a patient of FIG. 5 evidencing better functioning of vascular endothelium compared to patient of FIG. 3, with smaller return rate.

Also, functioning of vascular endothelium can be compared between smoking and non-smoking patient of the similar age: smoking 26 year-old patient of FIG. 5 shows smaller return rate to the stationary state and thus worse functioning of vascular endothelium compared to non-smoking 28 years-old patient of FIG. 6.

The invention claimed is:

1. A method for determination of parameters for evaluating vascular endothelium function in a human subject, the method comprising:
    (a) measuring and recording as a function of time the intensity of one NADH fluorescence emission wavelength signal emitted from skin tissue cells in a selected location on an upper limb of said subject to obtain a baseline, wherein said NADH fluorescence signal is emitted upon illumination with and absorption of one wavelength of UV exciting light;
    (b) blocking blood flow in an artery to the upper limb upstream to the selected location, while continuing measuring and recording said intensity as it grows up as a function of time;
    (c) releasing the block of blood flow while continuing measuring and recording said intensity as it changes as a function of time until obtaining a stationary state; and
    (d) determining parameters indicative of endothelial function from the course of changes of said intensity, the parameters being one or more selected from the group consisting of:
    the difference $\Delta l$ between the maximum level of intensity of NADH fluorescence signal upon blocking blood flow and the minimum level of intensity of NADH fluorescence after releasing the block of blood flow in step (c);
    the difference $\Delta l_1$ between the baseline intensity of NADH fluorescence signal in step (a) prior to blocking blood flow and the maximum level of intensity of NADH fluorescence signal upon said blocking blood flow in stet (b); and
    the difference $\Delta l_2$, between the minimum level of intensity of NADH fluorescence signal and the stationary state of intensity of NADH fluorescence signal after releasing the block of blood flow in step (c).

2. The method of claim 1 wherein the selected location is a forearm or hand.

3. The method of claim 1 which further comprises determining the half-time $t_{1/2}$ required for increase of intensity of NADH fluorescence signal from its minimum level after releasing the block of blood flow in step (b) by a half of the difference $\Delta l_2$ between the minimum level and the stationary state of intensity of NADH fluorescence signal after releasing the block of blood flow.

4. The method of claim 1 which further comprises determining the time $t_g$ between releasing the block of blood flow and reaching the stationary state of the intensity of NADH fluorescence signal in step (c).

5. The method of claim 1 wherein said blocking and releasing blood flow is obtained by tightening and releasing, respectively, a restriction means around said upper limb.

6. The method of claim 5 wherein said restriction means is an inflatable restriction means.

7. The method of claim 6 wherein said inflatable restriction means is a pressure cuff.

8. The method of claim 1 wherein said NADH fluorescence is obtained by illumination of said upper limb with the exciting light in the wavelength range from 300 to 400 nm.

9. The method of claim 8 wherein said the exciting light has the wavelength of about 350 nm.

10. The method of claim 1 wherein said NADH fluorescence signal is measured in the wavelength range from 420 to 480 nm.

11. The method of claim 10 wherein said NADH fluorescence signal, is measured at about 460 nm.

12. A system for evaluation of vascular endothelium function in a human subject, said system comprising
a means for illumination of a skin tissue of an upper limb of said subject with UV exciting light;
a means for measuring intensity of fluorescence signal emitted from the skin upon illumination with and absorption of UV exciting light and for recording changes of said intensity of the fluorescence signal over time, including measuring and recording as a function of time the intensity of one NADH fluorescence emission wavelength signal emitted from skin tissue cells in a selected location on an upper limb of said subject to obtain a baseline and measurement data, wherein said NADH fluorescence signal is emitted upon illumination with and absorption of one wavelength of UV exciting light;
a restriction means for blocking and releasing blood flow in an artery in the upper limb of said subject, including subsequent to obtaining the baseline, blocking blood flow in an artery on the upper limb upstream to the selected location, while said means for measuring continues measuring and recording said intensity as it grows as a function of time and releasing the block of blood flow while said means for measuring continues measuring and recording said intensity as it changes as a function of time until obtaining a stationary state;
a processor means for determining parameters indicative of endothelial function from the course of changes of said intensity, the parameters being one or more selected from the group consisting of:
the difference $\Delta l_1$ between the maximum level of intensity of NADH fluorescence signal upon blocking blood flow and the minimum level of intensity of NADH fluorescence after releasing the block of blood flow;
the difference $\Delta l_1$ between the baseline intensity of NADH fluorescence signal prior to blocking blood flow and the maximum level of intensity of NADH fluorescence signal upon said blocking blood flow; and
the difference $\Delta l_2$ between the minimum level of intensity of NADH fluorescence signal and the stationary state of intensity of NADH fluorescence signal after releasing the block of blood flow.

13. The system of claim 12 wherein said UV exciting light has the wavelength in the range from 300 to 400 nm.

14. The system of claim 13 wherein said UV exciting light has the wavelength of about 350 nm.

15. The system of claim 12 wherein said NADH fluorescence signal is measured in the wavelength range from 420 to 480 nm.

16. The system of claim 15 wherein said NADH fluorescence signal is measured at about 460 nm.

17. The system of claim 12 wherein the selected location is a forearm or hand.

18. The system of claim 12 wherein said processor means further determines the half-time $t_{1/2}$ required for increase of intensity of NADH fluorescence signal from its minimum level after releasing the block of blood flow by a half of the difference $\Delta l_2$ between the minimum level and the stationary state of intensity of NADH fluorescence signal after releasing the block of blood flow.

19. The system of claim 12 wherein said processor means further determines the time $t_g$ between releasing the block of blood flow and reaching the stationary state of the intensity of NADH fluorescence signal.

20. The system of claim 12 wherein said restriction means is an inflatable restriction means.

21. The system of claim 20 wherein said inflatable restriction means is a pressure cuff.

* * * * *